United States Patent [19]

Somogyvari et al.

[11] Patent Number: 5,557,023
[45] Date of Patent: Sep. 17, 1996

[54] OLEFIN OLIGOMERIZATION IN THE PRESENCE OF NOVEL COMPLEXES

[75] Inventors: Arpad F. Somogyvari, Calgary; Beth L. Creed, Airdrie; Antonio P. Nicola, Calgary; Alan R. Sanger, Edmonton; David J. Law, Edmonton; Ronald G. Cavell, Edmonton, all of Canada

[73] Assignee: The Governors of the University of Alberta, Edmonton, Canada

[21] Appl. No.: 447,887

[22] Filed: May 23, 1995

[51] Int. Cl.[6] .................. C07C 2/24; C07C 2/02
[52] U.S. Cl. .............. 585/513; 585/510; 585/511; 585/512; 585/514; 585/515; 585/520; 585/526; 585/527; 585/528; 585/530; 585/531
[58] Field of Search ................. 585/510, 511, 585/512, 513, 514, 515, 520, 526, 527, 528, 530, 531

[56] References Cited

U.S. PATENT DOCUMENTS

| | | | |
|---|---|---|---|
| 4,187,197 | 2/1980 | Kabanov et al. | 502/117 |
| 4,533,651 | 8/1985 | Masters et al. | 502/117 |
| 4,954,125 | 9/1990 | Ono et al. | 502/117 |
| 5,210,360 | 5/1993 | Wu | 585/511 |
| 5,286,696 | 2/1994 | Wu | 502/155 |
| 5,334,791 | 8/1994 | Cavell et al. | 585/277 |

FOREIGN PATENT DOCUMENTS

WO83/02907  9/1983  WIPO.

*Primary Examiner*—Asok Pal
*Assistant Examiner*—E. D. Irzinski
*Attorney, Agent, or Firm*—Kenneth H. Johnson

[57] ABSTRACT

The present invention relates to the oligomerization of lower alpha olefins, and particularly ethylene, to higher olefins in the presence of a catalyst precursor having either or both of a dithiophosphinate complex and a heterobifunctional ligand having a phosphine center and an imine or similar center, in the presence of an activator. The catalysts have a high reactivity and a good selectivity.

40 Claims, No Drawings

OLEFIN OLIGOMERIZATION IN THE PRESENCE OF NOVEL COMPLEXES

FIELD OF THE INVENTION

The present invention relates to a process for the oligomerization of lower olefins to one or more higher olefins, preferably alpha olefins. The oligomerization is carried out in the presence of a homogeneous catalyst comprising:

a) a catalyst precursor selected from the group consisting of:
1) dithiophosphinate (sometimes also called dithiophosphonates, typically when the P is substituted by an alkoxy radical) complexes of Ni, Cr, Ti, Zr, Hf, V, W, and Mo; and
2) complexes of Ni, Cr, Ti, Ni, Zr, Hf, V, W, and Mo with a heterobifunctional ligand having a phosphine center and an imine or similar center; and
3) complexes of Cr, Ti, Ni, Zr, Hf, V, W, and Mo having one or more ligands selected from the group consisting of dithiophosphinate ligands and heterobifunctional ligands having a phosphine center and an imine or similar center; and
b) an activator.

The oligomerization has a high conversion and a high degree of selectivity to the target product.

BACKGROUND OF THE INVENTION

The oligomerization of lower alpha olefins is of industrial concern as many polymers of alpha olefins such as ethylene and propylene comprise a higher alpha olefin such as butene, hexene or octene. If ethylene could be selectively oligomerized at relatively high conversion to a higher alpha olefin such as butene, hexene or octene it would mean that a plant need only have one monomer, such as ethylene, from which co-monomers could be produced.

There have been a number of attempts to oligomerize alpha olefins into higher alpha olefins.

There are a number of papers and patents in which Kingsley John Cavell and/or Anthony J. Masters is/are named as an author(s) (e.g. WO 8302907) in which square planar complexes of $Ni^{2+}$ are used to oligomerize alpha olefins. The complexes contain triphenyl phosphine and 2,4-pentanedithione (sacsac) or 4-thioxo-2-pentanone. These compounds are not the dithiophosphinate precursors of the present invention.

U.S. Pat. No. 4,533,651 issued Aug. 6, 1985 assigned to Commonwealth Scientific and Industrial Research Organization, Australia, also discloses oligomerization of ethylene with a nickel complex which contains a phosphine. The patent does not suggest the use of a ligand which contains both a phosphine and an imine or a dithiophosphinate ligand of the present invention.

Related U.S. Pat. No. 5,286,696 issued Feb. 14, 1994 and 5,210,360 issued May 11, 1993 both assigned to Phillips disclose the oligomerization of ethylene using a nickel complex which contains a phosphine. The patents do not disclose the presence of both a phosphine and an imine group or a dithiophosphinate in the ligand.

U.S. Pat. No. 5,334,791 issued Aug. 2, 1994 to Ligands, Inc. discloses that some of the catalyst precursors of the present invention may be used to hydrogenate non-aromatic unsaturated hydrocarbons. U.S. Pat. No. 5,352,813 issued Oct. 4, 1994 to the University of Alberta discloses that some of the catalyst precursors of the present invention may be used to carbonylate methanol. However, these patents do not disclose that such compounds in conjunction with an activator of a compound such as aluminum or boron could be used to oligomerize alpha olefins. Further these references do not teach or suggest that such an oligomerization if possible would have a high conversion and a controllable selectivity.

SUMMARY OF THE INVENTION

The present invention provides a process for the oligomerization of one or more $C_{2-4}$ olefins to one or more higher olefins comprising;

i) forming a dissolved catalyst system comprising:
a) a dissolved catalyst precursor selected from the group consisting of:
1) dithiophosphinate complexes of Cr, Ti, Ni, Zr, Hf, V, W, and Mo;
2) complexes of Cr, Ti, Ni, Zr, Hf, V, W, and Mo with a heterobifunctional ligand having a phosphine center and an imine or similar center; and
3) complexes of Cr, Ti, Ni, Zr, Hf, V, W, and Mo having one or more ligands selected from the group consisting of dithiophosphinate ligands and heterobifunctional ligands having a phosphine center and an imine or similar center; and
b) a soluble activator selected from the group consisting of activators of the formula $AlR_{(3-n)}X_n$ in which R is a $C_{1-8}$ alkyl radical, X is a halogen atom and n is 0, 1, or 2; alkyl aluminoxane compounds in which the alkyl group has from 1 to 8 carbon atoms and boron trihalide, tetraphenylborate and tri-or tetra(pentafluorophenyl) boron compounds or complexes, in a mole ratio of activator to catalyst precursor from 1:2 to 500:1 in a solvent selected from the group comprising $C_{6-12}$ cyclic aliphatic and aromatic compounds which are unsubstituted or substituted with a $C_{1-4}$ alkyl radical; and ii) contacting said olefin in liquid form with the solution of the catalyst at a temperature from −15° C. to 250° C.; and at a pressure from 15 to 1500 psi.

DETAILED DESCRIPTION

The catalyst precursor includes a source of a transition metal selected from the group consisting of Cr, Ti, Ni, Zr, Hf, V, W, and Mo, most preferably Ni, Cr, and Ti and either a dithiophosphinate ligand or a heterobifunctional ligand having a phosphine center and an imine center, or both. Preferred transition metals are nickel (Ni) and chromium (Cr).

The catalyst precursor may be a dithiophosphinate complex (i.e. a) 1).

The dithiophosphinate catalyst precursor has the formula:

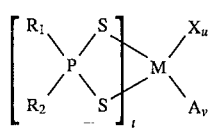

COMPLEX I wherein: M is selected from the group consisting of the above noted metals, preferably Ni, Cr, Ti, V, and Zr, t, u, and v are integers and the sum of 2t+u+v is the coordination number of M and t is an integer from 1 to half the coordination number of M and u and v may be 0 or integers, and the sum of u+v is from 0 to two less than the coordination number of M, $R_1$, and $R_2$, are independently selected from the group consisting of $C_{1-10}$ straight chained, branched or cyclic alkyl radicals; $C_{6-8}$ monoaromatic aryl radicals which are unsubstituted or substituted by up to three substituents selected from the group consisting of $C_{1-8}$ alkyl radicals; $C_{1-6}$ alkoxy or thioalkyl radicals; $C_{6-12}$ aryloxy radicals; $C_{6-12}$ arylthio radicals; $CF_3$; and fluorine; or if taken together $R_1$ and $R_2$ form a cyclic diradical (e.g. a divalent radical) of the formula:

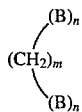

wherein n may independently be 0 or 1, m is an integer from 1 to 10, preferably 2 to 10, and each B may be independently selected from the group consisting of O or S;

X is selected from the group consisting of Cl, Br, I, and H; and

A is a ligand selected from the group consisting of:

i) ligands of the formula $P(R_3)_3$ wherein $R_3$ may be independently selected from the group of radicals consisting of $C_{1-10}$ straight chained, branched or cyclic alkyl radicals; $C_{6-8}$ monoaromatic aryl radicals which are unsubstituted or substituted by up to three, preferably one, substituents selected from the group consisting of $C_{1-8}$ alkyl radicals; and ii) ligands of the formula

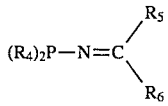

wherein $R_4$ may be a radical selected from the group of radicals from which R3 is selected and $R_5$ and $R_6$ may independently be a hydrogen atom or a radical selected from the group consisting of $C_{1-10}$ straight chained, or branched alkyl radicals; $C_{5-8}$ cyclic alkyl radicals, $C_{6-8}$ monoaromatic aryl radicals which are unsubstituted In the above catalyst precursors, preferably X is Cl or Br.

If $R_1$ and $R_2$ are taken together to form a diradical of the formula:

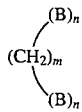

wherein n may independently be 0 or 1, m is an integer from 1 to 10, preferably 2 to 10 and each B may be independently selected from the group consisting of O or S, preferably $R_1$ and $R_2$ are independently selected from the group consisting of $C_{1-8}$ straight chained, branched or cyclic alkyl radicals; $C_{6-8}$ monoaromatic aryl radicals which are unsubstituted or substituted by a $C_{1-4}$ alkyl radical; $C_{1-6}$ alkoxy or thioalkyl radicals; $CF_3$; and fluorine.

In the above complexes the ligand A is preferably selected from the group of ligands consisting of:

i) ligands of the formula $P(R_3)_3$ where in $R_3$ may be independently selected from the group of radicals consisting of $C_{1-8}$ straight chained, branched or cyclic alkyl radicals; $C_{6-8}$ monoaromatic aryl radicals which are unsubstituted or substituted by a $C_{1-4}$ alkyl radical;

ii) ligands of the formula:

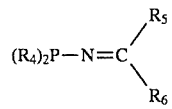

wherein $R_4$ may be a radical selected from the group consisting of radicals from the group consisting of $C_{1-8}$ straight chained, branched or cyclic alkyl radicals; $C_{6-8}$ monoaromatic aryl radicals which are unsubstituted or substituted by a $C_{1-4}$ alkyl radical and $R_5$ and $R_6$ may independently be a hydrogen atom or a radical selected from the group consisting of $C_{1-8}$ straight chained, branched or cyclic alkyl radicals; $C_{6-8}$ monoaromatic aryl radicals which are unsubstituted or substituted by a $C_{1-4}$ alkyl radical.

The catalyst precursor may contain a heterobifunctional ligand (i.e. i) a) 2).

The catalyst precursor having a heterobifunctional ligand having a phosphine center or an arsenic and an imine center has the general formula:

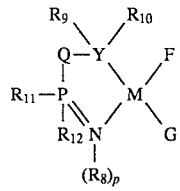

COMPLEX II wherein: M, is as defined above; $R_9$, $R_{10}$, $R_{11}$, and $R_{12}$ are independently selected from the group consisting of $C_{1-10}$ straight chained, branched or cyclic alkyl radicals; $C_{6-8}$ monoaromatic aryl radicals which are unsubstituted or substituted by up to three substituents, preferably one, selected from the group consisting of $C_{1-8}$ preferably $C_{1-4}$ alkyl radicals; F and G are independently selected from the group consisting of Cl, Br, I, and H, and ligands selected from the group consisting of:

i) ligands of the formula $P(R_3)_3$ where in $R_3$ may independently selected from the group of radicals consisting of $C_{1-10}$ straight chained, branched or cyclic alkyl radicals; $C_{6-8}$ monoaromatic aryl radicals which are unsubstituted or substituted by up to three preferably one, substituents selected from the group consisting of $C_{1-8}$ preferably $C_{1-4}$ alkyl radicals; and ii) ligands of the formula

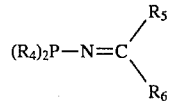

wherein $R_4$ may be a radical selected from the group of radicals from which $R_3$ is selected and $R_5$ and $R_6$ may independently be a hydrogen atom or a radical selected from the group consisting of $C_{1-10}$ preferably $C_{1-4}$ straight chained, or branched alkyl radicals; $C_{5-8}$ cyclic alkyl radicals, $C_{6-8}$ monoaromatic aryl radicals which are unsubstituted or substituted by a up to three, preferably only one, substituents selected from the group consisting of $C_{1-8}$ preferably $C_{1-4}$ alkyl radicals;

Y is P or As (preferably P), Q is selected from the group consisting of $(CH_2)_n$ wherein n is 1, 2, or 3, a $C_{2-4}$ alkyl radical, a disubstituted $C_6$ aryl radical, and $R_7N$ wherein $R_7$ is selected from the group consisting of $C_{1-6}$ straight chained or branched alkyl radicals, $C_{6-10}$ aryl radicals which are unsubstituted by a $C_{1-4}$ alkyl radical, and p is 0 or 1, if present $R_8$ is selected from the group consisting of:

i) a radical of the formula

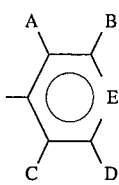

wherein A, B, C, D, are independently selected from the group consisting of F, H, $NO_2$, a $C_{1-6}$ alkyl radical, and a $C_{8-12}$ aryl radical, and E is an endocyclic nitrogen atom or a C—CN radical or isomers thereof, ii) $SiR^1R^2R^3$ wherein $R^1$, $R^2$, and $R^3$ are independently selected from the group consisting of $C_{1-4}$ alkyl radicals; and iii) a group of the formula

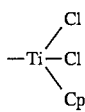

in which Cp is a cyclopentadienyl radical.

In the above ligands/complexes preferably M is Cr, Ti and Ni. Suitable ligands include those of the formula $Ph_2PCH_2CH_2PPh_2$=$NSiMe_3$ (i.e. Y is P, Q is —$CH_2CH_2$—, and $R_8$ is trimethyl silyl); and

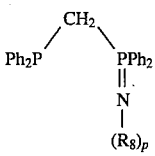

wherein p is 0 or 1, Q is $CH_2$ and if present $R_8$ is selected from the group as defined above.

Suitable ligands also include:

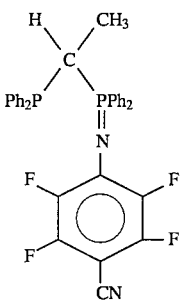

1-(N-4-cyanotetrafluorophenyl-diphenylphosphoranimine)-1-(diphenylphosphino)ethane (i.e. Q is CH—$CH_3$, p is 1 and $R_8$ is tetrafluorocyanophenyl);

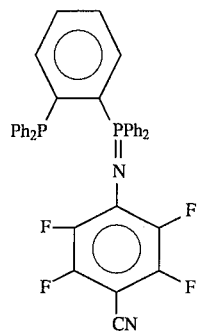

1-(N-4-cyanotetrafluorophenyldiphenylphosphoranimine)-2-(diphenylphosphino)benzene (i.e. p is 1, Q is a disubstituted (divalent) phenyl radical, and $R_8$ is tetrafluorocyanophenyl);

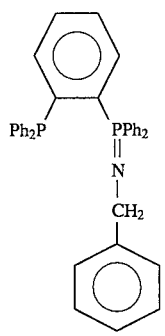

1-(N-benzyldiphenylphosphoranimine)-2-(diphenylphosphino)benzene (i.e. p is 1, Q is a disubstituted (divalent) phenyl radical, and $R_8$ is benzyl);

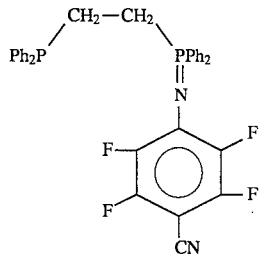

1-( N-4-cyanotetrafluorophenyldiphenylphosphoranimine)-2-(diphenylphosphino)ethane (i.e. p is 1, Q is —$CH_2CH_2$—(e.g. an ethylene diradical), and $R_8$ is tetrafluorocyanophenyl);

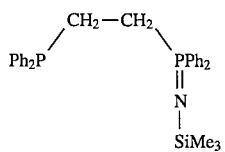

1-diphenylphosphino-2-(N-trimethylsilyldiphenylphosphoranimine)ethane (i.e. Q is —$CH_2CH_2$—, p is 1 and $R_8$ is trimethyl silyl);

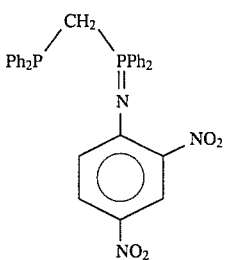

N-2,4-di(nitro)phenyl(diphenylphosphoranimine)methylenediphenylphosphine (i.e. Q is —CH$_2$—, p is 1 and R$_8$ is 2,4-dinitrophenyl)

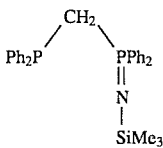

1-diphenylphosphino-1-(N-trimethylsilyldiphenylphosphanimine)methane (i.e. Q is —CH$_2$—, p is 1 and R$_8$ is trimethyl silyl)(in the above specific formulae R$_9$, R$_{10}$, R$_{11}$, and R$_{12}$ are all phenyl radicals); and

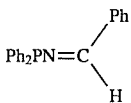

N-diphenylphosphinobenzylimine.

The catalyst precursor may be of the formula

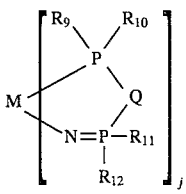
COMPLEX III wherein M, X, and Q are as defined above; j is 2 or 3 depending on the coordination number of M; and R$_9$, R$_{10}$, R$_{11}$, and R$_{12}$ are independently selected from the group consisting of C$_{1-10}$ straight chained, branched or cyclic alkyl radicals; C$_{6-8}$ monoaromatic aryl radicals which are unsubstituted or substituted by up to three substituents, preferably one, selected from the group consisting of C$_{1-8}$, preferably C$_{1-4}$, alkyl radicals.

The catalyst precursor may be of the formula

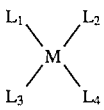
COMPLEX IV wherein L$_1$, L$_2$, L$_3$, and L$_4$ are independently selected from the group consisting of
  i) ligands of the formula

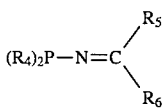

wherein R$_4$ may be a radical selected from the group of radicals from which R$_3$ is selected and R$_5$ and R$_6$ may independently be a hydrogen atom or a radical selected from the group consisting of C$_{1-10}$, straight chained, or branched alkyl radicals; C$_{5-8}$ cyclic alkyl radicals, C$_{6-8}$ monoaromatic aryl radicals which are unsubstituted or substituted by up to three, preferably one, substituents selected from the group consisting of C$_{1-8}$, preferably C$_{1-4}$ alkyl radicals;

ii) or L$_1$ and L$_2$, or L$_3$ and L$_4$, or both, may be taken together to form a ligand of the formula

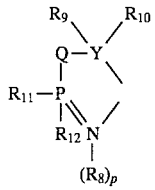

wherein Y, Q, R$_8$, R$_9$, R$_{10}$, R$_{11}$, and R$_{12}$, and p are as defined above:

iii) ligands of the formula P(R$_3$)$_3$ where in R$_3$ may be independently selected from the group of radicals consisting of C$_{1-10}$ straight chained, branched or cyclic alkyl radicals; C$_{6-8}$ monoaromatic aryl radicals which are unsubstituted or substituted by up to three, preferably one, substituents selected from the group consisting of C$_{1-8}$, alkyl radicals; and provided at least one of L$_1$, L$_2$, L$_3$, and L$_4$ is a ligand of formulas i) or ii) above;

iv) olefins selected from the group consisting of C$_{2-4}$ olefins, and C$_{6-8}$ cyclic, nonconjugated diolefins; and provided at least one of L$_1$, L$_2$, L$_3$, and L$_4$ is a ligand of formulas i) or ii) above.

Suitable olefins include ethylene, 1,5-cyclooctadiene (cod); and norbornadiene (nbd).

Preferably the catalyst precursor is a complex of the transition metal, preferably Ni, Cr, Ti, V, and Zr, most preferably Ni and the ligand.

The catalyst precursor is dissolved in a solvent in which the co-catalyst and the alpha olefin are also soluble or a solvent which is miscible with solvents for the co-catalyst and alpha olefin. Typically the solvent is a C$_{6-12}$ cyclic aliphatic or aromatic compound which is unsubstituted or substituted by up to six substituents selected from the group consisting of C$_{1-4}$ alkyl radicals and halogen atoms. Suitable solvents include cyclohexane, toluene and chlorobenzene.

The activator for the catalyst is typically an aluminum alkyl compound such as are used in Ziegler-Natta catalysts. The activator may be selected from the group of activators consisting of:

i) activators of the formula AlR$_{3-n}$X$_n$ wherein R is a C$_{1-8}$, preferably C$_{1-4}$, alkyl radical, most preferably an ethyl radical, X is halogen, preferably chlorine, and n is 0, 1 or 2;

ii) C$_{1-8}$, preferably C$_{1-4}$ alkyl, most preferably methyl aluminoxane compounds; and iii) boron trifluoride.

Commercially available activators include diethyl aluminum chloride (DEAC), ethyl aluminum dichloride (EADC), methyl aluminoxane (MAO) and boron trifluoride.

The degree of oligomerization is controlled by the mole ratio of activator to catalyst precursor which may range from 1:2 to 500:1, preferably from 5:1 to 250:1.

The olefin may be used in the form of a condensed liquid depending on the pressure and temperature (i.e. for ethylene the temperature must be below 9° C. for the monomer to be a liquid) of the process or more generally in the form of a solution of olefin in a solvent as noted above. Ethylene and propylene are prefered olefins.

The solution of catalyst precursor, activator and olefin are then reacted in a pressurized vessel (a Parr bomb, autoclave or a reactor (CSTR)) at a temperature from −15° C. to 250°

C., preferably from 0 to 250° C., and for the nickel complexes most preferably from 0° to 30° C. The pressure in the reactor may be from 15 to 1500 psi, preferably from 60 to 1200 psi. If the pressure and temperature are such to maintain the olefin in a liquid form then the olefin need not be dissolved in a solvent.

Typically the residence time in the reactor will be at least a half an hour. The reactants are all liquids and the process is homogeneous. On exiting the reactor the liquid phase may be subjected to conventional separation techniques such as distillation to separate the oligomerized olefin from the feed olefin.

One particular advantage of the process of the present invention is "high reactivity". The activity is typically not less than 1500 g of olefin per gram of catalyst per hour of residence time in the reactor. Further by selecting the catalyst precursor and activator it is possible to control the product distribution. For example, starting with ethylene the product may be 90+% of 1-butene.

The invention will be illustrated by the following non-limiting examples. In the examples unless otherwise indicated parts means parts by weight (e.g. grams). In the examples Ph is phenyl, Me is methyl, OEt is ethoxide, and Bu is butyl.

Catalyst Precursors

Dithiophosphinate Complexes:

[NiCl(PPh$_3$)(S$_2$PPh$_2$)] (A)

NiCl$_2$(PPh$_3$)$_2$ (1.645 g, 2.5 mmol) in ethanol (150 cm$^3$) was stirred under argon with NH$_4$[S$_2$PPh$_2$] (0.672 g, 2.5 mmol) for 0.5 hours. Fifty cm$^3$ of diethyl ether was added to the resulting solution which was then stirred for a further 10 minutes, after which the solution was filtered and washed with degassed diethyl ether (3×20cm$^3$). One hundred and fifty cm$^3$ of CH$_2$Cl$_2$ was added to the filtrate and the resulting mixture was further filtered to remove any inorganic salts. The compound was then recrystallized using a mixture of CH$_2$Cl$_2$/hexane. The yield was 1.18 g (76%).

[NiCl(PPh$_3$)(S$_2$PMe$_2$)] (B)

NiCl$_2$(PPh$_3$)$_2$ (10.00 g, 15 mmol) in toluene (300 cm$^3$) was stirred under argon with NaS$_2$PMe$_2$·2H$_2$O (2.67 g, 15 mmol) for 2.5 hours. The solution was cooled to −20° C. and filtered, the solid residue was washed with degassed diethyl ether (3×20 cm$^3$) and dried under vacuum for 0.5 hours. One hundred and fifty cm$^3$ of CH$_2$Cl$_2$ was added to the filtrate and the resulting mixture was further filtered to remove any inorganic salts. The compound was then recrystallized using a mixture of CH$_2$Cl$_2$ hexane. The yield was 3.46 g (47%).

[Ni(PPh$_3$)(S$_2$O(OEt)$_2$)$_2$] (C)

NiCl$_2$(PPh$_3$)$_2$ (1.00 g, 1.5 mmol) in dichloromethane (150 cm$^3$) was stirred under argon with NH$_4$[S$_2$P(OEt)$_2$] (2.76 g, 1.5 mmol) for 0.5 hours. The solution was filtered to remove inorganic salts. The dichloromethane was removed under vacuum and the resulting solid was redissolved in diethyl ether (20 cm$^3$). Slow evaporation of the solvent to approximately 5 cm$^3$ at room temperature resulted in the precipitation of the desired product. The compound was recrystallized using this method to remove any excess PPh$_3$. (Yield 0.69 g, 65%)

[Ni(S$_2$O(OEt)$_2$)$_2$] (D)

NiCl$_2$·6H$_2$O (0.238 g, 1.0 mmol) in absolute ethanol (50 cm$^3$) was stirred under argon with NH$_4$[S$_2$P(OEt)$_2$] (0.406 g, 2.0 mmol) for 1 hour. The resulting solution was filtered and the precipitate was dissolved in dichloromethane. The solution was washed with degassed water (3×20 cm$^3$) to remove inorganic salts. The organic layer was separated and the solvent removed under vacuum and the resulting solid was redissolved in hexane (20 cm$^3$). Slow evaporation of the solvent resulted in the precipitation of the desired product. The compound was recrystallized from hexane (cooling to −40° C.). (Yield 0.25 g, 58%)

[Ni(PPh$_3$)$_2$S$_2$OMe$_2$]$^+$BPh$_4$$^-$(E)

[NiCl$_2$(PPh$_3$)$_2$] (1 g, 1.53 mmol) NaS$_2$PMe$_2$ (0.116 g, 1.53 mmol) and NaBPh$_4$ (0.523 g, 1.53 mmol) were stirred in an acetonitrile solution (30 cm$^3$) under argon for 1 hour. The solution was filtered to remove NaCl and the solvent was removed under vacuum. Vigorous stirring of the residue with dry degassed hexane gave the product as a brown precipitate. (Yield 0.96 g, 63%)

[NiCl(PBu$_3$)(S$_2$PPh$_2$)] (F)

[NiCl$_2$(PPh$_3$)$_2$] (1.657 g, 3 mmol) in 150 cm$^3$ toluene was stirred under argon with NH$_4$[S$_2$PPh$_2$] (0.802 g, 3 mmol) for 0.5 hours. The solution was then filtered to remove inorganic salts. The toluene was removed under reduced pressure to yield a purple oil. The yield is nearly quantitative.

[NiCl(PBu$_3$)(S$_2$PMe$_2$)] (G)

[NiCl$_2$(PBu$_3$)$_2$] (1.657 g, 3 mmol) in 150 cm$^3$ of toluene were stirred under argon with NaS$_2$PMe$_2$·2H$_2$O (0.553 g, 3 mmol) for 2 hours. The solution was then filtered to remove inorganic salts. The toluene was removed under reduced pressure to give a high yield (80–90%) of a purple oil.

Phosphine Imine Complexes

[Ni(Ph$_2$P—N=CHPh)$_4$] (H)

Bis(1,5-cyclooctadiene)nickel (0.48 g, 1.76 mmol) and Ph$_2$P—N=CHPh (2.023 g, 6.99 mmol) were stirred as a suspension in hexane in a flask under an argon atmosphere at 0 C. Dichloromethane was slowly added to the suspension until solution occured and immediately a brown precipitate formed. After allowing the mixture to come to room temperature the precipitate was filtered and dried under vacuum to give a product sensitive to air and moisture: [Ni(Ph$_2$P—N=CHPh)$_4$] MMR$^{31}$P {$^1$H}CD$_2$Cl$_2$ δ74.4 ppm

[Ni(cod))Ph$_2$P—N=CHPh)$_2$] (cod=cyclooctadiene) (I)

Bis(1,5-cyclooctadiene)nickel(1.377 g, 5 mmol) and Ph$_2$P—N=CHPh (2.9 g, 10 mmol) were stirred as a suspension in hexane in a flask under an argon atmosphere at 0° C. Dichloromethane was slowly added to the suspension until solution occured and immediately a brown precipitate formed. After allowing the mixture to come to room temperature the precipitate was filtered and dried under vacuum to give a product sensitive to air and moisture:

[Ni(cod)(Ph$_2$P—N=CHPh)$_2$] NMR $^{31}$P {$^1$H} CD$_2$Cl$_2$ δ73.15 ppm.

[Ni(Ph$_2$PCH$_2$P(Ph)$_2$N—C$_6$F$_4$CN)$_2$]CH$_2$Cl$_2$ (J)

Bis(1,5-cyclooctadiene)nickel (0.387 g, 1.4 mmol) and Ph$_2$PCH$_2$P(Ph)$_2$=N—C$_6$F$_4$CN (1.53 g, 2.67 mmol) were stirred as a suspension in hexane (15 cm$^3$) in a flask under an argon atmosphere at 0° C. Dichloromethane (5 cm$^3$) was slowly added to the suspension until a brown solution formed from which there formed a red precipitate. After allowing the mixture to come to room temperature the precipitate was filtered and dried under vacuum to give an analytically pure product.

[Ni(cod)Ph$_2$PCH$_2$P(Ph$_2$)=N—C$_6$F$_4$CN].CH$_2$Cl$_2$ (K)

Bis(1,5-cyclooctadiene)nickel (1.347 g, 4.9 mmol) and Ph$_2$PCH$_2$P(Ph)$_2$=N—C$_6$F$_4$CN (2.8 g, 4.9 mmol) were stirred as a suspension in hexane (15 cm$^3$) in a flask under an argon atmosphere at 0° C. Dichloromethane (15 cm$^3$) was slowly added to the suspension until the suspension changed from yellow to red/brown. After allowing the mixture to come to room temperature the precipitate was filtered and dried under vacuum to give a pale red powder.

A series of oligomerizations was then carried out with some of the above catalyst precursors and diethyl aluminum chloride (DEAC) or ethyl aluminum dichloride (EADC) as the activator. The oligomerizations were carried out under a nitrogen containing olefin atmosphere. The yields of $C_4$, $C_6$, $C_8$, $C_{10}$, $C_{12}$, $C_{14}$, $C_{16}$, $C_{18}$, and polymer $C_{18+}$ expressed as percentages were measured. The results are set forth in table I. In the table: PRE is the catalyst precursor; ACT is the activator; PPE is ethylene partial pressure in pounds per square inch gauge (PSIG); Temp is the reaction temperature in ° C.; Ti is reaction time in hours; PPN is the nitrogen partial pressure in PSIG; Ratio is the mol/mol ratio of activator to catalyst precursor; C followed by a number is the wt % of that cut of carbon atoms in the product; and C18+ is the "polymer cut" (which was filtered out of the solution).

TABLE 1

| RUN | 1 | 2 | 3 | 4 | 5 | 6 | 7 | 8 | 9 | 10 | 11 | 12 |
|---|---|---|---|---|---|---|---|---|---|---|---|---|
| PRE | A | A | A | A | H | H | H | H | H | H | I | A |
| ACT | DEAC | DEAC | DEAC | EADC | DEAC | DEAC | DEAC | DEAC | EADC | DEAC | DEAC | DEAC |
| PPE | 30 | 60 | 30 | 60 | 30 | 60 | 30 | 60 | 60 | 400 | 400 | 100 |
| Temp | 15 | 15 | 25 | 15 | 15 | 15 | 15 | 25 | 25 | 22 | 22 | 15 |
| Ti | 1 | 1 | 1 | 1 | 1 | 1 | 1 | 1 | 1 | 2 | 2 | 1 |
| PPN | 20 | 20 | 20 | 20 | 20 | 20 | 20 | 20 | 20 | 10 | 10 | 10 |
| Rato | 147 | 153 | 120 | 162 | 147 | 168 | 146 | 135 | 152 | 5.26 | 5.30 | 4.86 |
| C4 | 43.65 | 89.73 | 84.88 | 76.27 | 77.65 | 93.18 | 90.49 | 28.34 | 19.27 | 94.55 | 97.85 | 98.2 |
| C6 | 2.08 | 8.53 | 13.61 | 3.75 | 4.92 | 2.52 | 8.23 | 1.79 | 1.50 | 0.32 | 1.22 | 1.6 |
| C8 | 1.89 | 0.91 | 0.89 | 2.08 | 1.73 | 0.24 | 0.46 | 0.45 | 0.51 | 3.40 | 0.49 | 0.2 |
| C10 | 6.32 | 0.25 | 0.15 | 2.94 | 8.37 | 0.58 | 0.13 | 39.87 | 8.05 | 1.26 | 0.41 | 0.0 |
| C12 | 11.63 | 0.22 | 0.19 | 7.79 | 4.94 | 0.82 | 0.22 | 6.51 | 37.18 | (1) | (1) | (1) |
| C14 | 14.36 | 0.10 | 0.08 | 3.60 | 0.86 | 0.59 | 0.11 | 12.24 | 20.37 | (1) | (1) | (1) |
| C16 | 18.26 | 0.14 | 0.08 | 2.85 | 0.43 | 1.73 | 0.17 | 9.52 | 12.13 | (1) | (1) | (1) |
| C18 | 1.20 | 0.00 | 0.00 | 0.21 | 0.00 | 0.00 | 0.00 | 0.53 | 0.69 | (1) | (1) | (1) |
| C18+ | 0.58 | 0.13 | 0.13 | 0.51 | 1.09 | 0.34 | 0.19 | 0.22 | 0.30 | 1.26 | 0.02 | 0.1 |

(1) not determined

The initial activity of the catalyst system could exceed 400,000 moles of $C_2$ consumed permole of catalyst per hour. In some cases the $C_{10+}$ fraction may contain aromatic components possibly from a reaction with the solvent.

A further series of experiments was then run. The results of these experiments are set out in tables 2 and 3 in which the same abbreviations are used.

TABLE 2

| RUN | 1 | 2 | 3 | 4 | 5[2] | 6[3] | 7 | 8[4] | 9[5] | 10 | 11 | 12 |
|---|---|---|---|---|---|---|---|---|---|---|---|---|
| PRE | H | A | H | A | H | H | H | A | A | A | A | H |
| ACT | EADC | EADC | DEAC | EADC | DEAC | EADC | DEAC | DEAC | EADC | DEAC | DEAC | EADC |
| PPE | 30 | 60 | 60 | 30 | 30 | 60 | 30 | 30 | 60 | 60 | 60 | 30 |
| Temp | 15 | 25 | 15 | 25 | 15 | 25 | 25 | 25 | 15 | 15 | 25 | 25 |
| Ti | 1 | 0.5 | 0.5 | 1 | 1 | 1 | 0.5 | 1 | 1 | 1 | 0.5 | 0.5 |
| PPN | 20 | 20 | 20 | 20 | 20 | 20 | 20 | 20 | 20 | 20 | 20 | 20 |
| Rato | 159 | 144 | 155 | 143 | 140 | 141 | 148 | 153 | 153 | 135 | 144 | 150 |
| C4 | 73.09 | 76.89 | 95.99 | 73.75 | 91.39 | 33.09 | 91.70 | 88.74 | 87.01 | 91.96 | 92.46 | 67.3 |
| C6 | 6.47 | 5.02 | 2.97 | 6.26 | 5.35 | 3.18 | 6.55 | 9.79 | 5.96 | 6.71 | 6.46 | 6.47 |
| C8 | 1.12 | 1.83 | 0.26 | 2.39 | 0.65 | 0.61 | 0.83 | 0.67 | 0.60 | 0.66 | 0.51 | 0.99 |
| C10 | 2.74 | 4.04 | 0.02 | 4.04 | 0.04 | 8.08 | 0.03 | 0.16 | 1.82 | 0.23 | 0.07 | 6.70 |
| C12 | 7.16 | 5.98 | 0.24 | 7.80 | 1.07 | 39.65 | 0.33 | 0.23 | 2.08 | 0.17 | 0.18 | 9.62 |
| C14 | 3.46 | 3.03 | 0.10 | 3.18 | 0.47 | 9.90 | 0.10 | 0.14 | 1.21 | 0.12 | 0.09 | 4.24 |
| C16 | 4.50 | 2.27 | 0.19 | 2.35 | 0.75 | 4.94 | 0.14 | 0.11 | 1.06 | 0.12 | 0.13 | 3.86 |
| C18 | 0.13 | 0.21 | 0.00 | 0.06 | 0.00 | 0.24 | 0.00 | 0.00 | 0.09 | 0.00 | 0.00 | 0.14 |
| C18+ | 1.33 | 0.72 | 0.22 | 0.18 | 0.27 | 0.32 | 0.31 | 0.17 | 0.16 | 0.02 | 0.11 | 0.73 |

[2] repeat of table 1 #5,
[3] repeat of table 1 #6,
[4] repeat of table 1 #3, and
[5] repeat of table 1 #4.

TABLE 3

| RUN | 13 | 14 | 15[6] | 16 |
|---|---|---|---|---|
| PRE | A | H | H | A |
| ACT | EDAC | EADC | DEAC | DEAC |
| PPE | 30 | 60 | 60 | 30 |
| Temp | 15 | 15 | 25 | 15 |
| Ti | 0.5 | 0.5 | 1 | 0.5 |
| PPN | 20 | 20 | 20 | 20 |
| Rato | 134 | 144 | 146 | 157 |
| C4 | 64.96 | 69.44 | 94.03 | 91.2 |
| C6 | 2.82 | 3.41 | 5.01 | 7.90 |
| C8 | 0.88 | 0.69 | 0.32 | 0.37 |
| C10 | 6.20 | 7.86 | 0.04 | 0.05 |
| C12 | 16.37 | 8.62 | 0.18 | 0.12 |
| C14 | 4.84 | 2.69 | 0.08 | 0.05 |
| C16 | 3.48 | 2.87 | 0.17 | 0.06 |
| C18 | 0.04 | 0.00 | 0.00 | 0.00 |
| C18+ | 0.39 | 4.42 | 0.17 | 0.19 |

[6]the amount of catalyst is double that of table 1 #8.

In the examples of the subject matter of the present invention it was observed that isomerization could be controlled by pressure. That is at ethylene pressures greater than 100 psig, typically from 100 to 400 psig, preferably from 100 to 200 psig, there tended to be higher amounts of the 1- higher olefin. Typically in the runs of oligomerization using the catalysts of the present invention the lowest selectivity for the preparation of 1-butene was from about 3 to 10% (runs 1, 2, 3, 4, 7, from table 1, and 2, 4, 7, 8, 9, 10, from table 2 and run 13 and 16 from table 3. The selectivity of the other runs except for runs 10 and 11 of table 1 ranged from 10 to 25%, while in runs 10 and 11 of table 1 the selectivity of 1-butene was about 80% and 60%, respectively. For comparative purposes the catalyst of example 1 of U.S. Pat. No. 4,533,651 was prepared and activated over a comparable ratio of DEAC and EADC (105 to 199) and oligomerization of ethylene was carried out under comparable times, temperatures and pressures. In all of the comparative runs of U.S. Pat. No. 4,533,651 the selectivity for 1-butene was in the 2 to 5% range.

The catalysts of the present invention can be controlled by pressure and the ratio of the activator to the catalysts to produce higher amounts of higher olefins and to be more selective in producing 1- or alpha olefins.

What is claimed is:

1. A process for the oligomerization of one or more $C_{2-4}$ olefins to one or more higher olefins comprising;

a) forming a solution of a catalyst comprising an activator and a catalyst precursor in a mole ratio from 1:1 to 500:1 in a solvent selected from the group consisting of $C_{6-12}$ cyclic aliphatic and aromatic compounds which are unsubstituted or substituted by a $C_{1-4}$ alkyl radical wherein said catalyst precursor is selected from the group consisting of:

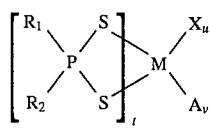

COMPLEX I wherein:

M is selected from the group consisting of Ni, Cr, Ti, V, Zr, Hf, W; and Mo; t, u, and v are integers, the sum of 2t+u+v is the coordination number of M, t is an integer from 1 to half the coordination number of M, u and v may be 0 or integers and the sum of u+v is from 0 to two less than the coordination number of M;

$R_1$, and $R_2$, are independently selected from the group consisting of $C_{1-10}$ straight chained, branched or cyclic alkyl radicals, $C_{6-8}$ monoaromatic aryl radicals which are unsubstituted or substituted by up to three substituents selected from the group consisting of $C_{1-8}$ alkyl radicals, $C_{1-6}$ alkoxy or thioalkyl radicals, $C_{6-12}$ aryloxy radicals, $C_{6-12}$ arylthio radicals, $CF_3$; and fluorine; or if taken together $R_1$ and $R_2$ form a diradical of the formula:

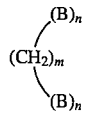

wherein each n is independently 0 or 1; m is an integer from 1 to 10; each B is independently selected from the group consisting of O or S; X is selected from the group consisting of Cl, Br, I, and H, and A is a ligand selected from the group consisting of:

i) ligands of the formula $P(R_3)_3$ wherein $R_3$ may independently be selected from the group of radicals consisting of $C_{1-10}$ straight chained, branched or cyclic alkyl radicals; $C_{6-8}$ monoaromatic aryl radicals which are unsubstituted or substituted by up to three substituents selected from the group consisting of $C_{1-8}$ alkyl radicals; and ii) ligands of the formula:

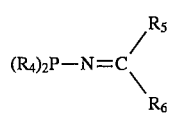

wherein $R_4$ may be a radical selected from the group of radicals from which $R_3$ is selected; and $R_5$ and $R_6$ may independently be a hydrogen atom or a radical selected from the group consisting of $C_{1-10}$ straight chained or branched alkyl radicals, $C_{5-8}$ cyclic alkyl radicals, and $C_{6-8}$ monoaromatic aryl radicals which are unsubstituted or substituted by up to three, substituents selected from the group consisting of $C_{1-8}$ alkyl radicals;

(2) complexes of a heterobifunctional ligand having a phosphine center and an imine center of the formula:

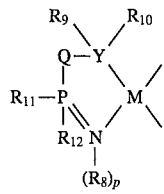

COMPLEX II wherein: M is as defined above;

$R_9$, $R_{10}$, $R_{11}$, and $R_{12}$ are independently selected from the group consisting of $C_{1-10}$ straight chained, branched or cyclic alkyl radicals, $C_{6-8}$ monoaromatic aryl radicals which are unsubstituted or substituted by up to three substituents selected from the group consisting of $C_{1-8}$ alkyl radicals;

F and G are independently selected from the group consisting of Cl, Br, I, and H, and ligands selected from the group consisting of:

i) ligands of the formula $P(R_3)_3$ where in $R_3$ is as defined above; and ii) ligands of the formula:

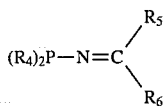

wherein $R_4$, $R_5$ and $R_6$ are as defined above; Y is P or As;

Q is selected from the group consisting of $(CH_2)_n$ wherein n is 1, 2, or 3, a $C_{2-4}$ alkyl radical, a disubstituted $C_6$ aryl radical, $R_7N$ wherein $R_7$ is selected from the group consisting of $C_{1-6}$ straight chained or branched alkyl radicals, $C_{6-10}$ aryl radicals which are unsubstituted or substituted by a $C_{1-4}$ alkyl radical; p is 0 or 1; and if present $R_8$ is selected from the group consisting of:

i) a radical of the formula:

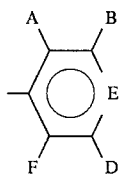

wherein A, B, C, D, are independently selected from the group consisting of F, H, $NO_2$, a $C_{1-6}$ alkyl radical, and a $C_{8-12}$ aryl radical, and E is an endocyclic nitrogen atom or a C—CN radical or isomers thereof;

ii( $SiR^1R^2R^3$ where in $R^1$, $R^2$, and $R^3$ are independently selected from the group consisting of $C_{1-4}$ alkyl radicals; and iii) a group of the formula:

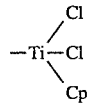

in which Cp is a cyclopentadienyl radical;

(3) complexes of the formula:

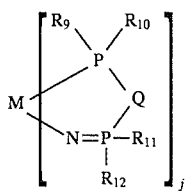     COMPLEX III wherein M, X, and Q are as defined above;

j is 2 or 3 depending on the coordination number of M; and $R_9$, $R_{10}$, $R_{11}$, and $R_{12}$ are independently selected from the group consisting of $C_{1-10}$ straight chained, branched or cyclic alkyl radicals; and $C_{6-8}$ monoaromatic aryl radicals which are unsubstituted or substituted by up to three substituents selected from the group consisting of $C_{1-8}$ alkyl radicals; and (4) complexes of the formula:

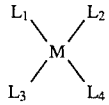     COMPLEX IV wherein M is as defined above, and $L_1$, $L_2$, $L_3$, and $L_4$ are independently selected from the group consisting of:

i) ligands of the formula:

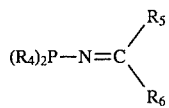

wherein R4, $R_5$ and $R_6$ are as defined above $L_1$ and $L_2$, or $L_3$ and $L_4$, or both, may be taken together to form a ligand of the formula:

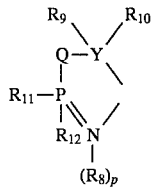

wherein Y, Q, R8, $R_9$, $R_{10}$, $R_{11}$, and $R_{12}$, and p are as defined above:

iii) ligands of the formula $P(R_3)_3$ where in $R_3$ is as defined above provided at least one of $L_1$, $L_2$, $L_3$, and $L_4$ is a ligand of formulas i) or ii) above; and iv) olefins selected from the group consisting of $C_{2-4}$ olefins, and $C_{6-8}$ cyclic, nonconjugated diolefins provided at least one of $L_1$, $L_2$, $L_3$, and $L_4$ is a ligand of formulas i) or ii) above;

and said activator selected from the group consisting of aluminum alkyl compounds of the formula $AiR_{(3-n)}X_n$ in which R is a $C_{1-8}$ alkyl radical, X is a halogen atom and n is 0, 1, or 2, alkyl aluminoxane compounds in which the alkyl group has from 1 to 8 carbon atoms, boron trihalide, tetraphenylborate, and tri- or tetra(penta fluorophenyl) boron compounds or complexes; and b) contacting said olefin in liquid form with the solution of the catalyst at a temperature from $-15°$ C. to $250°$ C.; and at a pressure from 15 to 1500 psi.

2. The process according to claim 1, wherein the temperature is from $0°$ C. to $250°$ C.

3. The process according to claim 2, wherein the mole ratio of activator to catalyst precursor is from 5:1 to 250:1.

4. The process according to claim 3, wherein the activator is selected from the group consisting of triethyl aluminum, diethyl aluminum chloride, ethyl aluminum dichloride, methyl aluminoxane, boron trifluoride, tetraphenylborate, and tri- or tetra(penta fluorophenyl) boron compounds or complexes.

5. The process according to claim 4, wherein the solvent for said catalyst is selected from the group consisting of cyclohexane and toluene.

6. The process according to claim 1, wherein the temperature is below $9°$ C. and said $C_{2-4}$ olefin is ethylene in liquid form.

7. The process according to claim 1, wherein the pressure is from 60 to 1200 psi and said $C_{2-4}$ olefin is ethylene dissolved in a solvent which is the same as the solvent for said catalyst or miscible with the solvent for said catalyst.

8. The process according to claim 6, wherein said catalyst precursor is a dithiophosphinate complex wherein X is Cl or Br, and $R_1$ and $R_2$ are independently selected from the group consisting of $C_{1-8}$ straight chained, branched or cyclic alkyl radicals; $C_{6-8}$ monoaromatic aryl radicals which are unsubstituted or substituted by a $C_{1-4}$ alkyl radical; $C_{1-6}$ alkoxy or thioalkyl radicals; $CF_3$; and fluorine or if taken together $R_1$ and $R_2$ form a diradical of the formula:

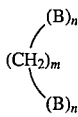

wherein n may independently be 0 or 1, m is an integer from 2 to 10 and each B may be independently selected from the group consisting of O or S.

9. The process according to claim 7, wherein said catalyst precursor is a dithiophosphinate complex wherein X is Cl or Br, and $R_1$ and $R_2$ are independently selected from the group consisting of $C_{1-8}$ straight chained, branched or cyclic alkyl radicals; $C_{6-8}$ monoaromatic aryl radicals which are unsubstituted or substituted by a $C_{1-4}$ alkyl radical; $C_{1-6}$ alkoxy or thioalkyl radicals; $CF_3$; and fluorine or if taken together $R_1$ and $R_2$ form a diradical of the formula

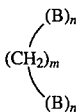

wherein n may independently be 0 or 1, m is an integer from 2 to 10 and each B may be independently selected from the group consisting of O or S.

10. The process according to claim 8, wherein said catalyst precursor is a dithiophosphinate complex and A is a ligand of the formula $P(R_3)_3$ wherein $R_3$ may independently selected from the group of radicals consisting of $C_{1-8}$ straight chained, branched or cyclic alkyl radicals; $C_{6-8}$ monoaromatic aryl radicals which are unsubstituted or substituted by a $C_{1-4}$ alkyl radical.

11. The process according to claim 9, wherein said catalyst precursor is a dithiophosphinate complex and A is a ligand of the formula $P(R_3)_3$ wherein $R_3$ may independently be selected from the group of radicals consisting of $C_{1-8}$ straight chained, branched or cyclic alkyl radicals; $C_{6-8}$ monoaromatic aryl radicals which are unsubstituted or substituted by a $C_{1-4}$ alkyl radical.

12. The process according to claim 8, wherein said catalyst precursor is a dithiophosphinate complex and A is a ligand of the formula:

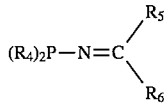

wherein $R_4$ may be a radical selected from the group consisting of radicals from the group consisting of $C_{1-8}$ straight chained, branched or cyclic alkyl radicals; $C_{6-8}$ monoaromatic aryl radicals which are unsubstituted or substituted by a $C_{1-4}$ alkyl radical and $R_5$ and $R_6$ may independently be a hydrogen atom or a radical selected from the group consisting of $C_{1-8}$ straight chained, branched or cyclic alkyl radicals; $C_{6-8}$ monoaromatic aryl radicals which are unsubstituted or substituted by a $C_{1-4}$ alkyl radical.

13. The process according to claim 9, wherein said catalyst precursor is a dithiophosphinate complex and A is a ligand of the formula:

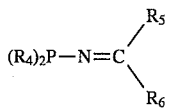

wherein $R_4$ may be a radical selected from the group consisting of radicals from the group consisting of $C_{1-8}$ straight chained, branched or cyclic alkyl radicals; $C_{6-8}$ monoaromatic aryl radicals which are unsubstituted or substituted by a $C_{1-4}$ alkyl radical and $R_5$ and $R_6$ may independently be a hydrogen atom or a radical selected from the group consisting of $C_{1-8}$ straight chained, branched or cyclic alkyl radicals; $C_{6-8}$ monoaromatic aryl radicals which are unsubstituted or substituted by a $C_{1-4}$ alkyl radical.

14. The process according to claim 6, wherein the catalyst precursor has the formula:

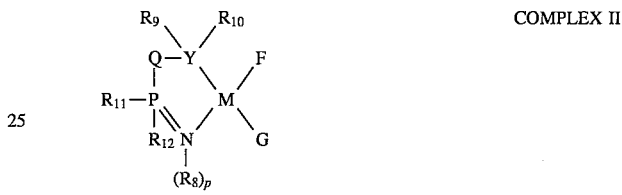

COMPLEX II wherein: M is selected from the group consisting of Ni, Cr, Ti, V, and Zr; $R_9$, $R_{10}$, $R_{11}$, and $R_{12}$ are independently selected from the group consisting of $C_{1-10}$ straight chained, branched or cyclic alkyl radicals; $C_{6-8}$ monoaromatic aryl radicals which are unsubstituted or substituted by a substituents selected from the group consisting of $C_{1-4}$ alkyl radicals; F and G are independently selected from the group consisting of Cl, Br, I and H; and ligands selected from the group consisting of:

i) ligands of the formula $P(R_3)_3$ where in $R_3$ may independently be selected from the group of radicals consisting of $C_{1-10}$ straight chained, branched or cyclic alkyl radicals; $C_{6-8}$ monoaromatic aryl radicals which are unsubstituted or substituted a $C_{1-4}$ alkyl radical; and ii) ligands of the formula

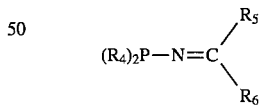

wherein $R_4$ may be a radical selected from the group of radicals from which $R_3$ is selected and $R_5$ and $R_6$ may independently be a hydrogen atom or a radical selected from the group consisting of $C_{1-4}$ straight chained, or branched alkyl radicals; $C_{5-8}$ cyclic alkyl radicals, $C_{6-8}$ monoaromatic aryl radicals which are unsubstituted or substituted by a $C_{1-4}$ alkyl radical;

Y is P or As, Q is selected from the group consisting of $(CH_2)_n$ wherein n is 1 or 2, a $C_{2-4}$ alkyl radical, and disubstituted $C_6$ aryl radical, and p is 0 or 1, if present $R_8$ is selected from the group consisting of:

i) a radical of the formula:

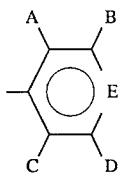

wherein A, B, C, D, are independently selected from the group consisting of F, H, $NO_2$, a $C_{1-6}$ alkyl radical, and a $C_{8-12}$ aryl radical, and E is an ii) $SiR^1R^2R^3$ wherein $R^1$, $R^2$, and $R^3$ are independently selected endocyclic nitrogen atom or a C—CN radical or isomers thereof; from the group consisting of $C_{1-4}$ alkyl radicals; and iii) a group of the formula

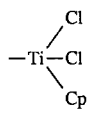

in which Cp is a cyclopentadienyl radical.

15. The process according to claim 7, wherein the catalyst precursor has the formula:

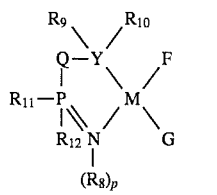

COMPLEX II wherein: M is selected from the group consisting of Ni, Cr, Ti, V, and Zr; $R_9$, $R_{10}$, $R_{11}$, and $R_{12}$ are independently selected from the group consisting of $C_{1-10}$ straight chained, branched or cyclic alkyl radicals; $C_{6-8}$ monoaromatic aryl radicals which are unsubstituted or substituted by a substituents selected from the group consisting of $C_{1-4}$ alkyl radicals; F and G are independently selected from the group consisting of Cl, Br, I and H; and ligands selected from the group consisting of:

i) ligands of the formula $P(R_3)_3$ where in $R_3$ may independently be selected from the group of radicals consisting of $C_{1-10}$ straight chained, branched or cyclic alkyl radicals; $C_{6-8}$ monoaromatic aryl radicals which are unsubstituted or substituted a $C_{1-4}$ alkyl radical; and ii) ligands of the formula

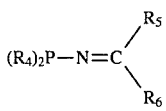

wherein $R_4$ may be a radical selected from the group of radicals from which $R_3$ is selected and $R_5$ and $R_6$ may independently be a hydrogen atom or a radical selected from the group consisting of $C_{1-4}$ straight chained, or branched alkyl radicals; $C_{5-8}$ cyclic alkyl radicals, $C_{6-8}$ monoaromatic aryl radicals which are unsubstituted or substituted by a $C_{1-4}$ alkyl radical;

Y is P or As, Q is selected from the group consisting of $(CH_2)_n$ wherein n is 1 or 2, a $C_{2-4}$ alkyl radical, and disubstituted $C_6$ aryl radical, and p is 0 or 1, if present $R_8$ is selected from the group consisting of:

i) a radical of the formula:

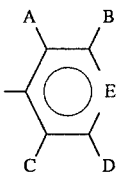

wherein A, B, C, D, are independently selected from the group consisting of F, H, $NO_2$, a $C_{1-6}$ alkyl radical, and a $C_{8-12}$ aryl radical, and E is an endocyclic nitrogen atom or a C—CN radical or isomers thereof;

ii) $SiR^1R^2R^3$ wherein $R^1$, $R^2$, and $R^3$ are independently selected from the group consisting of $C_{1-4}$ alkyl radicals; and iii) a group of the formula

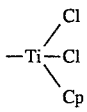

in which Cp is a cyclopentadienyl radical.

16. The process according to claim 14, wherein Y is P, o is O and Q is $CH_2$.

17. The process according to claim 15, wherein Y is P, p is O and Q is $CH_2$.

18. The process according to claim 14, wherein Y is P, p is O and Q is CH—$CH_3$.

19. The process according to claim 15, wherein Y is P, p is O and Q is CH—$CH_3$.

20. The process according to claim 14, wherein Y is P, p is O and Q is a disubstituted phenyl radical.

21. The process according to claim 15, wherein Y is P, p is O and Q is a disubstituted phenyl radical.

22. The process according to claim 14, wherein Y is P, p is 1, Q is CH—$CH_3$, and $R_8$ is a tetrafluorocyanophenyl radical.

23. The process according to claim 15, wherein Y is P, p is 1, Q is CH—$CH_3$, and $R_8$ is a tetrafluorocyanophenyl radical.

24. The process according to claim 14, wherein Y is P, p is 1, Q is a disubstituted phenyl radical, and $R_8$ is a tetrafluorocyanophenyl radical.

25. The process according to claim 15 wherein Y is P, p is 1, Q is a disubstituted phenyl radical, and $R_8$ is a tetrafluorocyanophenyl radical.

26. The process according to claim 14, wherein Y is P, p is 1, Q is a disubstituted phenyl radical, and $R_8$ is a benzyl radical.

27. The process according to claim 15, wherein Y is P, p is 1, Q is a disubstituted phenyl radical, and $R_8$ is a benzyl radical.

28. The process according to claim 16 wherein Y is P, p is 1, Q is an ethylene diradical, and $R_8$ is a tetrafluorocyanophenyl radical.

29. The process according to claim 15, wherein Y is P, p is 1, Q is an ethylene diradical, and $R_8$ is a tetrafluorocyanophenyl radical.

30. The process according to claim 14, wherein Y is P, p is 1, Q is an ethylene diradical, and $R_8$ is a trimethyl silyl radical.

31. The process according to claim 15, wherein Y is P, p is 1, Q is an ethylene diradical, and $R_8$ is a trimethyl silyl radical.

32. The process according to claim 16, wherein Y is P, p is 1, Q is a methylene radical, and $R_8$ is a trimethyl silyl radical.

33. The process according to claim 15, wherein Y is P, p is 1, Q is a methylene radical, and $R_8$ is a trimethyl silyl radical.

34. The process according to claim 14, wherein Y is P, p is 1, Q is a methylene radical, and $R_8$ is a 2,4-dinitrophenyl radical.

35. The process according to claim 15, wherein Y is P, p is 1, Q is a methylene radical, and $R_8$ is a 2,4-dinitrophenyl radical.

36. The process according to claim 6, wherein the catalyst precursor has the formula:

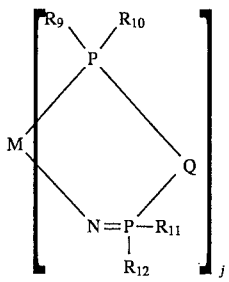

COMPLEX III wherein j is 2 or 3 depending on the coordination number of M; Q is selected from the group consisting of $(CH_2)_n$ wherein n is 1 or 2, a $C_{2-4}$ alkyl radical; and $R_9$, $R_{10}$, $R_{11}$, and $R_{12}$ are independently selected from the group consisting of $C_{1-10}$ straight chain, branched or cyclic alkyl radicals; $C_{6-8}$ monoaromatic aryl radicals which are unsubstituted or substituted by up to three substituents selected from the group consisting of $C_{1-8}$ alkyl radicals.

37. The process according to claim 7, wherein the catalyst precursor has the formula:

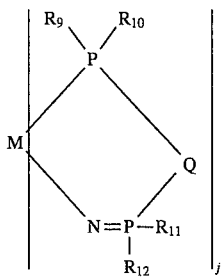

COMPLEX III wherein j is 2 or 3 depending on the coordination number of M; Q is selected from the group consisting of $(CH_2)_n$ wherein n is 1 or 2, a $C_{2-4}$ alkyl radical; and $R_9$, $R_{10}$, $R_{11}$, and $R_{12}$ are independently selected from the group consisting of $C_{1-10}$ straight chain, branched or cyclic alkyl radicals; $C_{6-8}$ monoaromatic aryl radicals which are unsubstituted or substituted by up to three substituents selected from the group consisting of $C_{1-8}$ alkyl radicals.

38. The process according to claim 6 wherein the catalyst precursor has the formula:

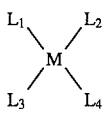

COMPLEX IV wherein M is as defined above, and $L_1$, $L_2$, $L_3$, and $L_4$ are independently selected from the group of consisting of:

i) ligands of the formula:

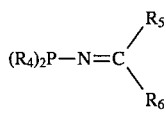

wherein $R_4$ may be a radical selected from the group of radicals from which $R_3$ is selected and $R_5$ and $R_6$ may independently be a hydrogen atom or a radical selected from the group consisting of $C_{1-10}$ straight chained, or branched alkyl radicals; $C_{5-8}$ cyclic alkyl radicals, $C_{6-8}$ monoaromatic aryl radicals which are unsubstituted or substituted by up to three substituents selected from the group consisting of $C_{1-8}$ alkyl radicals;

ii) or $L_1$ and L2, or $L_3$ and $L_4$, or both, may be taken together to form a ligand of the formula

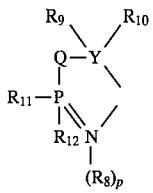

wherein Y is P or As, Q is selected from the group consisting of $(CH_2)_n$ wherein n is 1 or 2, a $C_{2-4}$ alkyl radical, $R_9$, $R_{10}$, $R_{11}$, and $R_{12}$, are independently selected from the group consisting of $C_{1-10}$ straight chained, branched or cyclic alkyl radicals; $C_{6-8}$ monoaromatic aryl radicals which are unsubstituted or substituted by a substituents selected from the group consisting of $C_{1-4}$, alkyl radicals; and p is 0 or 1 ,: if present $R_8$ is selected from the group consisting of:

i) a radical of the formula:

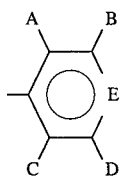

wherein A, B, C, D, are independently selected from the group consisting of F, H, $NO_2$, a $C_{1-6}$ alkyl radical, and a $C_{8-12}$ aryl radical, and E is an endocyclic nitrogen atom or a C—CN radical or isomers thereof;

ii) $SiR^1R^2R^3$ wherein $R^1$, $R^2$, and $R^3$ are independently selected from the group consisting of $C_{1-4}$ alkyl radicals; and iii) a group of the formula

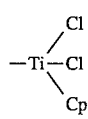

in which Cp is a cyclopentadienyl radical, iii) ligands of the formula $P(R_3)_3$ where in $R_3$ may be independently selected from the group of radicals consisting of $C_{1-10}$ straight chained, branched or cyclic alkyl radicals; $C_{6-8}$ monoaromatic aryl radicals which are unsubstituted or substituted by up to three substituents selected from the group consisting of $C_{1-8}$; alkyl radicals; and provided at least one of $L_1$, $L_2$, $L_3$, and $L_4$ is a ligand of formulas i) or ii) above;

iv) olefins selected from the group consisting of $C_{2-4}$ olefins, and $C_{6-8}$ cyclic, nonconjugated diolefins; and provided at least one of $L_1$, $L_2$, $L_3$, and $L_4$ is a ligand of formulas i) or ii) above.

39. The process according to claim 7 wherein the catalyst precursor has the formula:

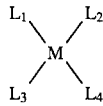

COMPLEX IV wherein M is as defined above, and $L_1$, $L_2$, $L_3$, and $L_4$ are independently selected from the group of consisting of:

i) ligands of the formula:

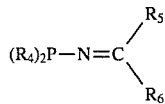

wherein $R_4$ may be a radical selected from the group of radicals from which $R_3$ is selected and $R_5$ and $R_6$ may independently be a hydrogen atom or a radical selected from the group consisting of $C_{1-10}$ straight chained, or branched alkyl radicals; $C_{5-8}$ cyclic alkyl radicals, $C_{6-8}$ monoaromatic aryl radicals which are unsubstituted or substituted by up to three substituents selected from the group consisting of $C_{1-8}$ alkyl radicals;

ii) or $L_1$ and $L_2$, or $L_3$ and $L_4$, or both, may be taken together to form a ligand of the formula

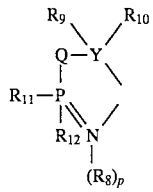

wherein Y is P or As, Q is selected from the group consisting of $(CH_2)_n$ wherein n is 1 or 2, a $C_{2-4}$ alkyl radical, $R_9$, $R_{10}$, $R_{11}$, and $R_{12}$, are independently selected from the group consisting of $C_{1-10}$ straight chained, branched or cyclic alkyl radicals; $C_{6-8}$ monoaromatic aryl radicals which are unsubstituted or substituted by a substituents selected from the group consisting of $C_{1-4}$, alkyl radicals; and p is 0 or 1,: if present $R_8$ is selected from the group consisting of:

i) a radical of the formula:

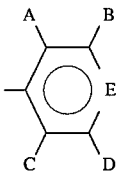

wherein A, B, C, D, are independently selected from the group consisting of F, H, $NO_2$, a $C_{1-6}$ alkyl radical, and a $C_{8-12}$ aryl radical, and E is an endocyclic nitrogen atom or a C—CN radical or isomers thereof;

ii) $SiR^1R^2R^3$ wherein $R^1$, $R^2$, and $R^3$ are independently selected from the group consisting of $C_{1-4}$ alkyl radicals; and iii) a group of the formula

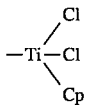

in which Cp is a cyclopentadienyl radical, iii) ligands of the formula $P(R_3)_3$ where in $R_3$ may be independently selected from the group of radicals consisting of $C_{1-10}$ straight chained, branched or cyclic alkyl radicals; $C_{6-8}$ monoaromatic aryl radicals which are unsubstituted or substituted by up to three substituents selected from the group consisting of $C_{1-8}$, alkyl ,radicals; and provided at least one of $L_1$, $L_2$, $L_3$, and $L_4$ is a ligand of formulas i) or ii) above;

iv) olefins selected from the group consisting of $C_{2-4}$ olefins, and $C_{6-8}$ cyclic, nonconjugated diolefins; and provided at least one of $L_1$, $L_2$, L3, and $L_4$ is a ligand of formulas i) or ii) above.

40. The process according to claim 5, wherein said catalyst precursor M is selected from the group consisting of Ni, Cr, Ti, V, and Zr.

* * * * *